United States Patent [19]
Nasser

[11] 3,974,679
[45] Aug. 17, 1976

[54] ACCELERATED CONCRETE STRENGTH TESTING

[75] Inventor: Karim W. Nasser, Saskatoon, Canada

[73] Assignee: Canadian Patents and Development Limited, Ottawa, Canada

[22] Filed: Sept. 2, 1975

[21] Appl. No.: 604,878

[52] U.S. Cl. ............................... 73/15.6; 73/88 C
[51] Int. Cl.² ........................................ G01N 3/10
[58] Field of Search ...................... 73/88 C, 15.6, 94

[56] References Cited
UNITED STATES PATENTS

| | | | |
|---|---|---|---|
| 1,985,598 | 12/1934 | Carver | 73/94 X |
| 2,697,938 | 12/1954 | Tanaka | 73/94 |
| 2,699,060 | 1/1955 | Safford | 73/94 X |
| 3,807,221 | 4/1974 | Brown et al. | 73/94 X |

*Primary Examiner*—Jerry W. Myracle
*Attorney, Agent, or Firm*—Ronald G. Bitner

[57] ABSTRACT

An accelerated strength testing method and apparatus for concrete in which a concrete mix sample is subjected to elevated temperature and pressure to accelerate curing. In the preferred embodiment, a prediction of 28-day strength is provided in about five hours. The apparatus comprises a container for the sample comprising a cylinder and a piston closure, means for applying force to the closure to pressurize the sample and seal the container, and heating means for heating the sample within the container.

7 Claims, 2 Drawing Figures

ACCELERATED CONCRETE STRENGTH TESTING

BACKGROUND OF THE INVENTION

This invention relates to accelerated strength testing of concrete.

With present practice, the quality of Portland cement concrete is based on the 28-day compressive strength of a specimen. However, in many concrete construction projects, a rapid and reliable prediction of the standard 28-day compressive strength would be advantageous. Early strength prediction can save expense by avoiding situations where the concrete does not reach the required design strength or by avoiding concrete that is unnecessarily strong. An accurate accelerated test of a concrete mix would allow rapid changes in the mix to be made to conform with specifications.

A number of methods for providing accelerated strength testing of a concrete mix have been proposed. The methods proposed include applying heat to specimen by means of saturated steam, hot water, autoclaving, dry oven heat, electrical heat or autogenously. None of these previously proposed methods have been found to be entirely satisfactory. In known methods which utilize heat to accelerate curing, a precuring step is commonly used to partially cure the specimen in order to prevent specimen separation in the subsequent heating step. However, this precuring step adds significantly to the time required. In proposed methods that attempt to provide early strength prediction, the ratio of the compressive strength to the standard 28-day strength is relatively low, and such methods, therefore, have low reliability, particularly when there are variations in the composition of the concrete mix.

SUMMARY OF THE INVENTION

An object of the present invention is to provide a compressive strength test for a concrete mix in a relatively short period of time.

Another object is to provide an accelerated strength test for a concrete mix that has a high correlation with the standard 28-day compressive strength test.

An object of the preferred embodiment of the present invention is to provide an accelerated strength test capable of providing a prediction of the compressive strength of a concrete mix in about five hours.

Another object is to provide a relatively simple accelerated compressive strength test for concrete suitable for field use.

Another object is to provide an accelerated strength test that is reliable for a variety of concrete mix compositions.

Another object is to provide an apparatus for carrying out an accelerated strength test.

Another object of the present invention is to provide an apparatus that can be used for ejecting the specimen from the container after curing, and performing the compressive strength test, in addition to providing the accelerated cured concrete specimens.

In accordance with the present invention a concrete mix sample is subjected to constant elevated pressure and elevated temperature, under predetermined conditions, to accelerate curing. It has been found that a high correlation exists between the resulting accelerated-cured compressive strength and the 28-day standard-cured strength which can be utilized to reliably predict the standard 28-day compressive strength.

The apparatus of the present invention comprises a container for receiving a sample of a concrete mix, comprising a cylinder and a removable closure having a piston and sealing means; means for pressing against the closure to pressurize the sample and maintain constant pressure; and heating means for heating the sample.

DESCRIPTION OF THE PREFERRED EMBODIMENT

Figure 1:
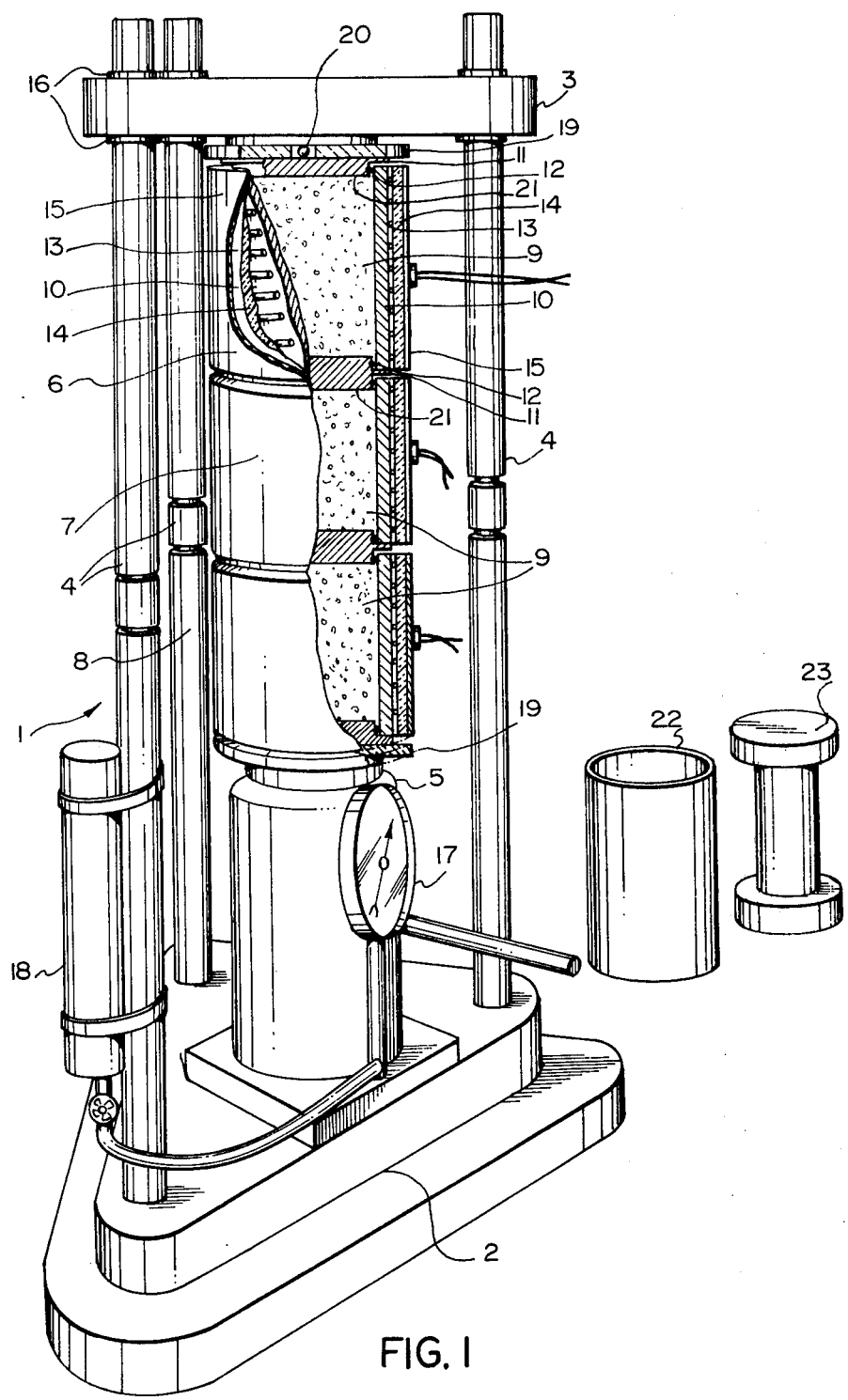
FIG. 1 is a partly sectioned, partly fragmented perspective view of the accelerated srength testing apparatus.

Referring to FIG. 1, the apparatus 1 comprises a frame, with base 2, head member 3 and interconnecting members 4; a hydraulic jack 5; and three concrete sample containers 6, 7 and 8.

Each sample container, for example, 6, comprises a cylinder 10 and removable closures 11 for each end. Each closure has a piston 21 around which an O-ring 12 is disposed to provide slidable sealing engagement with the inner walls of the cylinder 10.

Each container includes heating means in the form of electrical heating wiring 13 for heating the sample in the container. Surrounding each cylinder is insulating material 14 surrounded by a protective jacket 15.

Associated with the hydraulic jack 5 is a gauge 17, and an accumulator 18 that facilitates maintaining the sample under constant pressure.

Asbestos plates 19 are disposed, one beneath the bottom closure and one above the top closure, to avoid heat loss. A ball bearing 20 ensures proper alignment of the closures with the cylinders.

In order to make the apparatus adaptable for a different number of containers, the head member 3 is made vertically adjustable along the members 4 and locked by suitable means 16.

In operation, the containers 6, 7 and 8 are filled with the samples 9 and stacked with the closures 11 in place on top of the jack 5, as shown in FIG. 1. Extending the hydraulic jack 5 forces the containers upward against the frame head 3. The containers are filled sufficiently with the concrete mix sample so that piston 21 of the closure 11 applies direct pressure to the concrete mix as the jack 5 is extended. The jack 5 is loaded to a predetermined value. The accumulator 18 provides that the pressure remains at the predetermined value when the mix is subsequently heated. The O-ring provides sealing slidable engagment of the piston 21 within the cylinder 10.

Thereafter the heating means 13 are activated, subjecting the samples 9 to elevated temperature under predetermined conditions while pressure is maintained constant.

Pressurizing the sample prevents it from separating as it is heated. In previously proposed accelerated tests involving heating, in order to prevent separation or boiling, the sample is partially cured prior to the heating step. This precuring step consumes considerable time which is avoided by the present invention. Maintaining the sample at constant pressure facilitates consistent curing conditions for successive tests.

After the predetermined heating time has elapsed, heating is discontinued and the cured specimens are allowed to cool, or cooled mechanically. After cooling, the pressure of the jack is released and the containers removed.

The cured specimens may be ejected from the cylinder using components of the apparatus shown in FIG. 1. The ejecting apparatus includes an ejecting cylinder 22, slightly larger in diameter than the bore of the container cylinder, for engaging one end of a cylinder, with closures removed; and an ejecting member 23 having a diameter smaller than the bore of the container cylinder for pushing the specimens from the other end of the container when the three elements, i.e. the ejecting cylinder, a container and ejecting member, are placed in series between the jack and frame head.

The separated specimen may then be tested using a conventional compression strength test, again using components of the same apparatus. Since the compression tests must be performed on individual specimens, a spacer will be required between the top of the specimen and the frame head, or alternately, the frame head may be adjusted downward.

EXAMPLE

Sample containers were made, each comprising a steel cylinder, 3 inch inside diameter × 6½ inches long. The heating means comprised 25 gauge Nichrome wiring wound around the cylinder, drawing 100 watts of power. Around the electrical heating wiring was 1½ inches of insulation surrounded by a 6 inch diameter × 6½ inch long metal jacket. The upper and lower assembly included a ⅞ inch thick end closure, a 1 inch × 4 inch bearing plate and a ½ inch asbestos plate between the closure and bearing plate. The upper closure assembly included, in addition, a ball bearing between the closure and bearing plate. The closures each had reduced diameter portions which defined the pistons about which rubber O-rings, ⅛ × 2¾ inches, were applied for sealing with the inside surface of the respective cylinder end. The closures between cylinders were single units, 1¼ inches thick, adapted to seal two adjacent ends of two cylinders at the same time.

A plastic liner, greased on the outside, was placed in each of three containers. The closures were also greased. Each container was filled with the sample in three consecutive equal layers, each layer being rodded 25 times with a round-nosed ⅝ inch diameter rod. The containers were filled sufficiently so that the piston contacted the sample. The filled containers were stacked on the apparatus as shown in FIG. 1.

A pressure of 1500 psi was applied with the jack in conjunction with the accumulator to pressurize the sample and to seal the containers. Subsequently, the containers were plugged into an electrical source supplying 100 watts to each container.

Preliminary tests were made to establish a curing cycle which made the most economical and practical use of time and the strength development of concrete. It was previously decided that a total testing time of approximately five hours should be the ultimate goal.

With the apparatus described, the samples in the containers reached a maximum temperature of about 300°F within ½ hour. It was found that varying the heating time from 2½ to 4 hours, in intervals, showed substantial gains in accelerated strength up to 3 hours. However, periods longer than 3 hours displayed little additional strength gain. It was further found that the hot cured specimens had reduced strengths when the cooling period was less than 1½ hours. Moreover, cooling periods less than 2 hours yielded specimens too hot to be handled with bare hands. Because of the above considerations, the procedure for subsequent samples comprised a heating period of 3 hours and a cooling period of 2 hours at room temperature (70°F). After 2 hours of cooling, the temperature of the core of the specimen was 155°F.

After cooling, the pressure was released and the containers removed. The specimens were ejected from the cylinders using the same hydraulic jack and frame apparatus as the ejecting apparatus previously described. The uncapped specimens were then tested for compressive strength, again using the same jack and frame apparatus, the compressive strength being recorded from the gauge on the jack.

A variety of mixes were prepared. A sample of each mix was cured using the aforesaid acceleraed test method and apparatus. Another sample of each mix was cured in accordance with the standard 28-day procedure using 6 × 12 inch cylinders. The tests included a variety of aggregates, aggregate-cement ratios, water-cement ratios and admixtures. The proportions of the mix constituents are shown in the following table. The cement used was Type 1, Normal Portland cement. The coarse and fine aggregates for the normal weight aggregates of Series A, B and C, were from glacial-fluvial deposits in the Saskatoon, Saskatchewan area. The coarse and fine lightweight aggregates for Series F were an expanded clay shale. The air-entraining agent for Series D, E and F was a vinsol resin type. In Series E, fly ash was used in conjunction with the air-entraining agent. Fly ash, a commonly used pozzolan, acts as a water-reducing agent and set-retarding agent.

Figure 2:
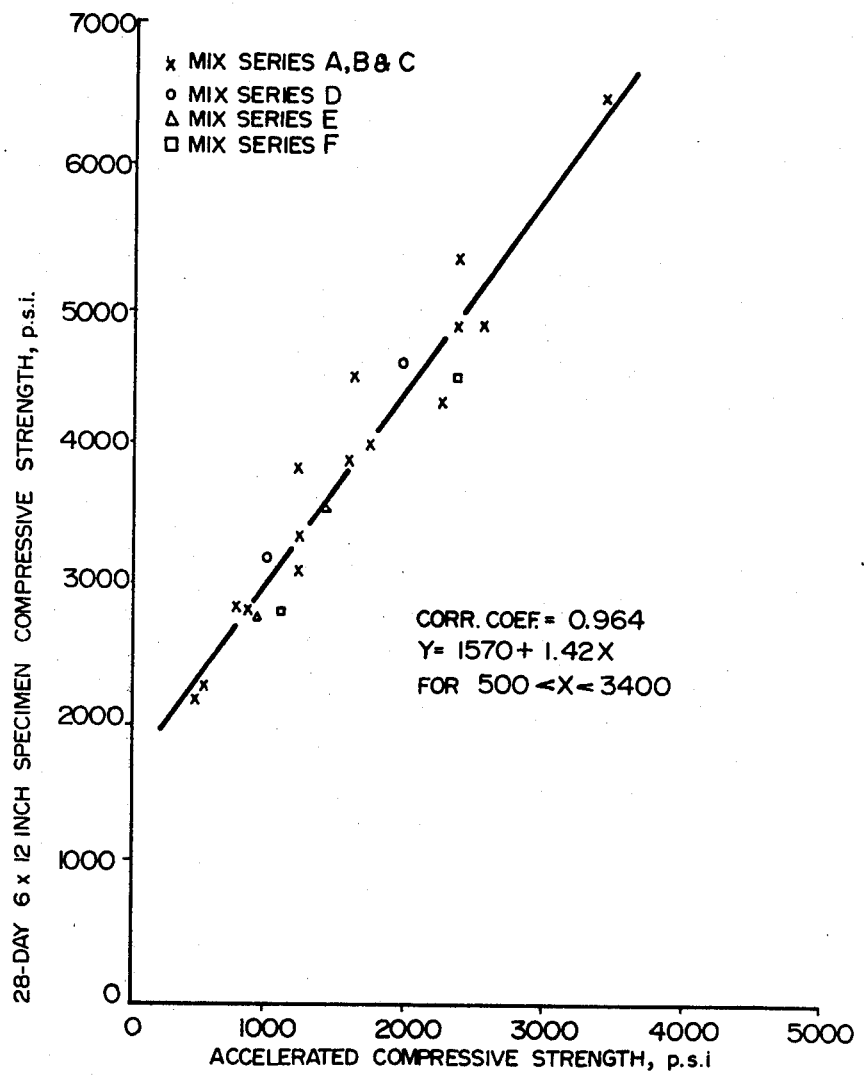
FIG. 2 is a graphic representation of the relationship between accelerated compressive strength and standard 28-day compressive strength.

The accumulated data is shown in FIG. 2. The data was analyzed using linear regression. The regression equation obtained was $y = 1570 + 1.42X$ for $500 < X < 3400$ where $Y$ = predicted 28-day standard cured compressive concrete strength (psi) and $X$ = measured accelerated compressive strength (psi). For all data the accuracy of prediction is within ±15%, while 81% of the results are within ±10%. The correlation coefficient is 0.964. The ratio of accelerated-cured to 28-day standard-cured compressive strengths varied from 24% to 52.5%. The ratio increased as the 28-day strength increased but did not affect the accuracy of the results.

| Mix Design No. | Aggregate Cement Ratio | Water Cement Ratio | Weight in Pounds | | | |
|---|---|---|---|---|---|---|
| | | | Water | Cement | Coarse Aggregate | Fine Aggregate |
| A1 | 5 | 0.45 | 21.6 | 48.0 | 144.3 | 96.0 |
| A2 | 5 | 0.50 | 20.0 | 40.0 | 120.0 | 80.0 |
| A3 | 5 | 0.55 | 21.8 | 39.6 | 119.0 | 79.5 |
| A4 | 5 | 0.60 | 23.6 | 39.4 | 118.0 | 78.8 |
| A5 | 5 | 0.65 | 25.4 | 39.0 | 78.2 | 117.0 |
| B1 | 7 | 0.55 | 16.7 | 30.4 | 127.5 | 85.3 |

-continued

| Mix Design No. | Aggregate Cement Ratio | Water Cement Ratio | Weight in Pounds | | | |
|---|---|---|---|---|---|---|
| | | | Water | Cement | Coarse Aggregate | Fine Aggregate |
| B2 | 7 | 0.60 | 18.1 | 30.2 | 126.8 | 84.5 |
| B3 | 7 | 0.65 | 19.5 | 30.1 | 126.1 | 84.1 |
| B4 | 7 | 0.70 | 20.9 | 29.9 | 125.6 | 83.6 |
| B5 | 7 | 0.75 | 22.3 | 29.8 | 124.8 | 83.2 |
| C1 | 9 | 0.70 | 17.0 | 24.3 | 131.5 | 87.5 |
| C2 | 9 | 0.75 | 18.2 | 24.2 | 131.0 | 87.0 |
| C3 | 9 | 0.80 | 19.3 | 24.1 | 130.0 | 86.5 |
| C4 | 9 | 0.85 | 21.4 | 24.0 | 129.3 | 86.2 |
| C5 | 9 | 0.90 | 21.5 | 23.8 | 128.7 | 85.8 |

| Mix Design No. | Aggregate Cement Ratio | Water Cement Ratio | Air Entraining Agent | Weight in Pounds | | | | |
|---|---|---|---|---|---|---|---|---|
| | | | | Water | Cement | Coarse Aggregate | Fine Aggregate | Flyash |
| D1 | 7 | 0.55 | 18 cc | 17.6 | 31.9 | 133.9 | 89.5 | |
| D2 | 7 | 0.65 | 18 cc | 20.5 | 31.5 | 132.5 | 88.5 | |
| E1 | 7 | 0.55 | 14 cc | 17.6 | 25.5 | 133.9 | 89.5 | 6.4 |
| E2 | 7 | 0.65 | 14 cc | 20.5 | 25.2 | 132.5 | 88.5 | 6.3 |
| F1 | 3.6 | 0.75 | 16 cc | 23.7 | 31.6 | 48.8 | 64.3 | |
| F2 | 3.6 | 0.88 | 17 cc | 27.0 | 30.6 | 47.0 | 62.5 | |

In the example, the parameters were chosen to provide a total testing time of 5 hours. However, it appears that the present invention can be adapted to provide useful prediction of compressive strength in the time range from 1 to 20 hours. For the shorter times, high temperature, high pressure, and mechanical cooling are required. The maximum pressure that can be applied is limited by the strength of the aggregate used. The minimum pressure that may be used will be determined by the highest temperature, and in particular, must be sufficient to prevent boiling of the sample. Although a pressure of about 1500 psi is preferred, it appears that a practical pressure range is from 500 to 2000 psi. A practical temperature range appears to be 200° to 800°F, but preferably about 300°F. With the shorter testing times, and relatively high pressure and temperature, the strength of the cured specimens will be a lower fraction of the 28-day strength and consequently have reduced reliability. For increased accuracy of strength prediction, lower temperature and pressure with longer curing times can be used. The preferred total testing time is in the range from 3 to 8 hours. It is important to note that altering any parameter such as, temperature, pressure, heating time or cooling time, requires establishing a new equation for correlating with 28-day strength.

Although, in the example, the heating step consisted of supplying a predetermined amount of electrical energy to the heating elements for a predetermined time, it will be appreciated that reproducible conditions may be provided by other means, for example, maintaining the sample at a predetermined temperature for a predetermined time. Similarly, the cooling procedure may be specified in a number of ways to provide consistent results.

The apparatus may be modified from that shown in FIG. 1. For example, the heating means may comprise an elongated heating element supported by the closure and adapted to be disposed coaxially within the container.

What is claimed is:

1. A method for accelerated strength testing of concrete comprising:

a. placing a concrete mix sample in a container and sealing the container;
   b. applying a predetermined pressure to the sample;
   c. supplying heat to the sample under predetermined conditions to raise the temperature thereof, while maintaining the pressure of the sample substantially constant;
   d. cooling the sample under predetermined conditions; and
   e. measuring the compressive strength of the sample.

2. The method of claim 1 wherein the sample is subjected to a pressure from 500 to 2,000 psi.

3. The method of claim 2 wherein the pressure is about 1500 psi, the heating temperature is about 300°F, and the total heating and cooling time is about 5 hours.

4. The method of claim 1 wherein the total heating and cooling time is from 1 to 20 hours.

5. The method of claim 4 wherein the total heating and cooling time is from 3 to 8 hours.

6. The method of claim 1 wherein the sample is heated to a temperature between 200° and 800°F.

7. An accelerated concrete strength testing apparatus comprising:

a. a container, for receiving a sample of a concrete mix, comprising a cylinder and a removable closure;
   b. said closure including a piston with sealing means for slidable sealing engagement with the inner walls of the cylinder;
   c. means for applying a predetermined force to the closure to pressurize the sample comprising a base member, a head member, an interconnecting member for fixing the head member with respect to the base member, a hydraulic jack for positioning between the base member and head member, and an accumulator associated with the hydraulic jack for maintaining constant pressure of the sample; and
   d. heating means for heating the concrete mix sample within the container under predetermined conditions to cure the concrete mix sample.

* * * * *